US012317893B2

(12) United States Patent
Lutz et al.

(10) Patent No.: US 12,317,893 B2
(45) Date of Patent: Jun. 3, 2025

(54) MULTIFUNCTIONAL NATURAL PROTECTANT SYSTEMS WITH HYDROXYACETOPHENONE

(71) Applicant: Lincoln Manufacturing Inc., North Kingstown, RI (US)

(72) Inventors: Patrick Jay Lutz, Nazareth, PA (US); Peter Hornish, Lincoln, RI (US)

(73) Assignee: Barentz North America, LLC, Avon, OH (US)

( * ) Notice: Subject to any disclaimer, the term of this patent is extended or adjusted under 35 U.S.C. 154(b) by 40 days.

(21) Appl. No.: 17/650,417

(22) Filed: Feb. 9, 2022

(65) Prior Publication Data

US 2022/0264875 A1 Aug. 25, 2022

Related U.S. Application Data

(60) Provisional application No. 63/203,808, filed on Jul. 30, 2021, provisional application No. 63/149,653, filed on Feb. 15, 2021.

(51) Int. Cl.

| A01N 35/04 | (2006.01) |
|---|---|
| A01N 25/22 | (2006.01) |
| A01N 25/24 | (2006.01) |
| A01N 31/02 | (2006.01) |
| A01P 1/00 | (2006.01) |
| A61P 31/00 | (2006.01) |
| A61P 31/04 | (2006.01) |

(52) U.S. Cl.
CPC ............. *A01N 35/04* (2013.01); *A01N 25/22* (2013.01); *A01N 25/24* (2013.01); *A01N 31/02* (2013.01); *A01P 1/00* (2021.08); *A61P 31/00* (2018.01); *A61P 31/04* (2018.01)

(58) Field of Classification Search
CPC ........ A01N 25/22; A01N 25/24; A01N 31/02; A01N 35/04; A01P 1/00; A61P 31/00; A61P 31/04
See application file for complete search history.

(56) References Cited

U.S. PATENT DOCUMENTS

| 8,226,931 | B2 | 7/2012 | Kindel et al. |
| 10,638,755 | B2 | 5/2020 | Pesaro et al. |
| 10,752,571 | B2 | 8/2020 | Pillai et al. |
| 2020/0071643 | A1 | 3/2020 | Cole et al. |

FOREIGN PATENT DOCUMENTS

| CA | 2907495 A1 * | 11/2014 | ........... A61K 31/197 |
| CN | 105025712 A * | 11/2015 | |
| CN | 108186510 A | 6/2018 | |
| CN | 109172388 A | 1/2019 | |
| CN | 109589297 A | 4/2019 | |
| CN | 110037973 A | 7/2019 | |
| CN | 110638742 A | 1/2020 | |
| CN | 110664633 A | 1/2020 | |
| CN | 111434330 A | 7/2020 | |
| CN | 111481465 A | 8/2020 | |
| CN | 108338965 B | 9/2020 | |
| CN | 111937874 A | 11/2020 | |
| CN | 111991319 A | 11/2020 | |
| EP | 2774481 A1 | 9/2014 | |
| WO | 2015144326 A1 | 10/2015 | |

OTHER PUBLICATIONS

CN105025712A—English translation (Year: 2015).*
International Search Report and Written Opinion received in PCT/US22/15756 dated May 17, 2022.

* cited by examiner

*Primary Examiner* — Umamaheswari Ramachandran
(74) *Attorney, Agent, or Firm* — Blank Rome LLP

(57) ABSTRACT

The present invention relates to the use of multifunctional protectants comprising (i) hydroxyacetophenone with (ii) at least one of natural 1,3-propanediol and a mastic extract to protect a formulation from biodegradation. The present invention also relates to the use of a protectant comprising (i) hydroxyacetophenone with (ii) at least one of vitamin B5, vitamin C, and vitamin E to protect a formulation from biodegradation.

2 Claims, No Drawings

MULTIFUNCTIONAL NATURAL PROTECTANT SYSTEMS WITH HYDROXYACETOPHENONE

This application claims the benefit of U.S. Provisional Application No. 63/203,808, filed Jul. 30, 2021, and U.S. Provisional Application No. 63/149,653, filed Feb. 15, 2021, each is which is hereby incorporated by reference.

FIELD OF THE INVENTION

The present invention relates to the use of multifunctional protectants comprising (i) hydroxyacetophenone with (ii) at least one of natural 1,3-propanediol and a mastic extract to protect a formulation from biodegradation. The present invention also relates to the use of a protectant comprising (i) hydroxyacetophenone with (ii) at least one of vitamin B5, vitamin C, and vitamin E to protect a formulation from biodegradation.

BACKGROUND

There are many drawbacks to currently available natural and naturally-derived antimicrobial formulations. They are expensive, and high concentrations of them (for instance, >2%) are often required to prevent microbial growth and preserve a product. Many have undesirable colors and odors, have poor stability (for example, in aqueous systems), and are not effective against a broad spectrum of microorganisms. Additionally, some such natural or naturally-derived antimicrobial mixtures cause thinning of formulations. Many are oils or extracts which limits their usage in various formulations.

U.S. Pat. No. 10,638,755 describes certain antimicrobial compositions comprising an acetophenone derivative and at least one second antimicrobial agent.

U.S. Pat. No. 10,752,571 is directed to methods of purifying crude 4-hydroxyacetophenone.

U.S. Pat. No. 8,226,931 is describes a mixture of compounds having the sensory properties of wintergreen.

International Publication No. WO 2015/144326 discloses a combination of one or more glycerol and/or oligoglycerol esters of branched chains and/or unbranched chains of alkane carboxylic acids and 4-hydroxyacetophenone.

There is a continuing need for low cost and safe natural preservative systems which are effective against a broad spectrum of microorganisms.

SUMMARY OF THE INVENTION

The protectants (such as natural protectants) of the present invention are relatively cheap to make, easy to work with and incorporate into finished products, generally have no odor, and have reduced (compared to prior oil preservative systems) or no color. In one embodiment, the protectant comprises (i) hydroxyacetophenone with (ii) at least one of 1,3-propanediol and a mastic extract (e.g., in an amount to protect a formulation or product from biodegradation). One preferred embodiment is a protectant comprising hydroxyacetophenone and 1,3-propanediol. Another preferred embodiment is a protectant comprising hydroxyacetophenone and mastic oil. Yet another is a protectant comprising hydroxyacetophenone and mastic water. Preferably, the protectant includes a synergistic amount of its components. For example, in one embodiment, the protectant comprises a synergistic amount of hydroxyacetophenone and 1,3-propanediol to inhibit microbial growth (e.g., fungi growth). In another embodiment, the protectant comprises a synergistic amount of hydroxyacetophenone and mastic oil to inhibit microbial growth (e.g., fungi growth). In yet another embodiment, the protectant comprises a synergistic amount of hydroxyacetophenone and mastic water to inhibit microbial growth (e.g., fungi growth). Each of these embodiments may optionally include one or more additional natural or naturally derived compounds (e.g., natural or naturally derived antioxidants) and/or one or more other antimicrobials. In one embodiment, when the protectant includes 4-hydroxyacetophenone and 1,3-propanediol, the protectant does not contain 3-phenylpropanol, 1,2-hexanediol, 1,2-octanediol, or ethylhexylglycerin. In another embodiment, the weight ratio of 4-hydroxyacetophenone and 1,3-propanediol is no more than 1:3 (e.g., the weight ratio can be 1:4 or 1:9). In yet another embodiment, the weight ratio of 4-hydroxyacetophenone and 1,3-propanediol ranges from about 10:90 to about 30:70, such as about 20:80.

One embodiment is a product comprising an effective amount of a protectant described herein. Another embodiment is a product comprising an effective amount of (i) hydroxyacetophenone with (ii) at least one of 1,3-propanediol and a mastic extract to inhibit microbial growth (e.g., fungi growth) in the product. In one embodiment, the product is not intended for oral administration to an animal.

Another embodiment is a protectant comprising (a) 4-hydroxyacetophenone, (b) 1,3-propanediol, and (c) ethylhexylglycerin, wherein the protectant does not contain 3-phenylpropanol. In yet another embodiment, the protectant does not contain 1,2-hexanediol or 1,2-octanediol. Preferably, the protectant includes a synergistic amount of its components. For example, in one embodiment, the protectant comprises a synergistic amount of 4-hydroxyacetophenone, 1,3-propanediol, and ethylhexylglycerin to inhibit microbial growth (e.g., fungi growth). In another embodiment, the weight ratio of 4-hydroxyacetophenone and 1,3-propanediol is no more than 1:3 (e.g., the weight ratio can be 1:4 or 1:9).

Yet another embodiment is a method of killing and/or inhibiting the growth of microorganisms (e.g., fungi) on a substrate by applying an effective amount of a protectant as described herein to the substrate. Yet another embodiment is a method of killing and/or inhibiting the growth of microorganisms (e.g., fungi) on a substrate by applying an effective amount of (i) hydroxyacetophenone with (ii) at least one of 1,3-propanediol and a mastic extract to the substrate. In one embodiment, when the method includes applying 4-hydroxyacetophenone and 1,3-propanediol, the method does not include applying 3-phenylpropanol, 1,2-hexanediol, 1,2-octanediol, or ethylhexylglycerin to the substrate.

Yet another embodiment is a concentrate comprising (or consisting essentially of, or consisting of) (i) hydroxyacetophenone with (ii) at least one of 1,3-propanediol and a mastic extract for inhibiting microbial growth (e.g., fungi growth). In one embodiment, the concentrate comprises (or consists essentially of, or consists of) (i) hydroxyacetophenone with (ii) at least one of 1,3-propanediol and a mastic extract and (iii) water. In another embodiment, the concentrate comprises (or consists essentially of, or consists of) (i) hydroxyacetophenone, (ii) 1,3-propanediol, and (iii) optionally, water. In yet another embodiment, the concentrate comprises (or consists essentially of, or consists of) (i) hydroxyacetophenone, (ii) mastic water, and (iii) optionally, water. In yet another embodiment, the concentrate comprises (or consists essentially of, or consists of) (i) hydroxyacetophenone, (ii) mastic oil, and (iii) optionally, water. In a preferred embodiment, the concentrate consists of (i) hydroxyacetophenone, (ii) 1,3-propanediol, and (iii) optionally, water. The weight ratio of 4-hydroxyacetophenone and 1,3-propanediol in the concentrate may range from about 10:90 to about 30:70, such as about 20:80. In a preferred embodiment, the concentrate consists of (i) from about 10 to about 30% by weight of hydroxyacetophenone and (ii) from about 70 to about 90% by weight of 1,3-propanediol. In a more preferred embodiment, the concentrate consists of (i) about 20% by weight of hydroxyacetophenone and (ii) about 80% by weight of 1,3-propanediol. In one embodiment, when the concentrate includes 4-hydroxyacetophenone and 1,3-propanediol, the concentrate does not contain 3-phenylpropanol, 1,2-hexanediol, 1,2-octanediol, or ethylhexylglycerin.

In one embodiment, the concentrate comprises (or consists essentially of, or consists of) (a) 4-hydroxyacetophenone, (b) 1,3-propanediol, and (c) ethylhexylglycerin, wherein the concentrate does not contain 3-phenylpropanol. For example, the concentrate may comprise from about 60 to about 80% by weight of 1,3-propanediol, from about 10 to about 25% by weight (such as from about 10 to about 20% by weight) of 4-hydroxyacetophenone, and from about 1 to about 15% by weight (such as from about 1 to about 10% by weight or from about 5 to about 15% by weight) of ethylhexylglycerin, based upon 100% total weight of concentrate. The concentrate may further comprise at least one of vitamin B5, vitamin C, and vitamin E, such as from about 1 to about 5% by weight of at least one of vitamin B5, vitamin C, and vitamin E. In a preferred embodiment, the concentrate comprises about 69% by weight of 1,3-propanediol, about 20% by weight of 4-hydroxyacetophenone, about 10% by weight of ethylhexylglycerin, and about 1% by weight of vitamin B5 (or DL-panthenol), based upon 100% total weight of concentrate.

4-hydoxyacetophenone degrades upon exposure to light, oxygen, and elevated temperatures resulting in a darkened substance. This can result in products containing 4-hydroxyacetophenone changing color (darkening) over time, which is not desired for such products as personal care products (e.g., shampoos). The present inventors surprisingly discovered that the degradation of 4-hydroxyacetophenone can be prevented by the inclusion of at least one of vitamin B5, vitamin C, and vitamin E. 4-hydroxyacetophenone with the at least one of vitamin B5, vitamin C, and vitamin E can be incorporated into a product as a protectant (such as a natural protectant). The protectants (such as natural protectants) of the present invention are relatively cheap to make, easy to work with and incorporate into finished products, generally have no odor, and have reduced (compared to prior oil preservative systems) or no color.

One embodiment is a protectant comprising (i) 4-hydroxyacetophenone, and (ii) at least one of vitamin B5, vitamin C, and vitamin E (e.g., in an amount to protect a formulation or product from biodegradation). In one embodiment, the protectant includes a sufficient amount of the at least one of vitamin B5, vitamin C, and vitamin E to prevent degradation of the 4-hydroxyacetophenone.

Another embodiment is a protectant comprising (i) 4-hydroxyacetophenone, (ii) at least one of vitamin B5, vitamin C, and vitamin E, and (iii) at least one of 1,3-propanediol and a mastic extract (e.g., in an amount to protect a formulation or product from biodegradation). One preferred embodiment is a protectant comprising (i) hydroxyacetophenone, (ii) at least one of vitamin B5, vitamin C, and vitamin E, and (iii) 1,3-propanediol. Another preferred embodiment is a protectant comprising (i) hydroxyacetophenone, (ii) at least one of vitamin B5, vitamin C, and vitamin E, and (iii) mastic oil. Yet another is a protectant comprising (i) hydroxyacetophenone, (ii) at least one of vitamin B5, vitamin C, and vitamin E, and (iii) mastic water. Preferably, the protectant includes a synergistic amount of its components. For example, in one embodiment, the protectant comprises a synergistic amount of hydroxyacetophenone, vitamin B5, and 1,3-propanediol to inhibit microbial growth (e.g., fungi growth). In another embodiment, the protectant comprises a synergistic amount of hydroxyacetophenone, vitamin B5, and mastic oil to inhibit microbial growth (e.g., fungi growth). In yet another embodiment, the protectant comprises a synergistic amount of hydroxyacetophenone, vitamin B5 and mastic water to inhibit microbial growth (e.g., fungi growth). In one embodiment, the protectant includes a sufficient amount of the at least one of vitamin B5, vitamin C, and vitamin E to prevent degradation of the 4-hydroxyacetophenone.

Each of these embodiments may optionally include one or more additional natural or naturally derived compounds and/or one or more other antimicrobials. In one embodiment, when the protectant includes 4-hydroxyacetophenone and 1,3-propanediol, the protectant does not contain 3-phenylpropanol, 1,2-hexanediol, 1,2-octanediol, or ethylhexylglycerin. In another embodiment, the weight ratio of 4-hydroxyacetophenone and 1,3-propanediol is no more than 1:3 (e.g., the weight ratio can be 1:4 or 1:9).

Another embodiment is a product comprising an effective amount of a protectant described herein. In one embodiment, the product comprises an effective amount of a protectant described herein. Another embodiment is a product comprising an effective amount of (i) hydroxyacetophenone with (ii) at least one of vitamin B5, vitamin C, and vitamin E to inhibit microbial growth (e.g., fungi growth) in the product. Another embodiment is a product comprising an effective amount of (i) hydroxyacetophenone, (ii) at least one of vitamin B5, vitamin C, and vitamin E, and (iii) at least one of 1,3-propanediol and a mastic extract to inhibit microbial growth (e.g., fungi growth) in the product. In one embodiment, the product is not intended for oral administration to an animal.

Yet another embodiment is a method of killing and/or inhibiting the growth of microorganisms (e.g., fungi) on a substrate by applying an effective amount of a protectant as described herein to the substrate. Yet another embodiment is a method of killing and/or inhibiting the growth of microorganisms (e.g., fungi) on a substrate by applying an effective amount of (i) hydroxyacetophenone, (ii) at least one of vitamin B5, vitamin C, and vitamin E, and (iii) optionally, at least one of 1,3-propanediol and a mastic extract to the substrate. In one embodiment, when the method includes applying 4-hydroxyacetophenone and 1,3-propanediol, the method does not include applying 3-phenylpropanol, 1,2-hexanediol, 1,2-octanediol, or ethylhexylglycerin to the substrate.

Yet another embodiment is a concentrate comprising (or consisting essentially of, or consisting of) (i) hydroxyacetophenone, and (ii) at least one of vitamin B5, vitamin C, and vitamin E for inhibiting microbial growth (e.g., fungi growth). The concentrate may include a sufficient amount of the at least one of vitamin B5, vitamin C, and vitamin E to prevent degradation of the 4-hydroxyacetophenone.

Yet another embodiment is a concentrate comprising (or consisting essentially of, or consisting of) (i) hydroxyacetophenone, (ii) at least one of vitamin B5, vitamin C, and vitamin E, and (iii) at least one of 1,3-propanediol and a mastic extract for inhibiting microbial growth (e.g., fungi growth). The concentrate may include a sufficient amount of the at least one of vitamin B5, vitamin C, and vitamin E to prevent degradation of the 4-hydroxyacetophenone. In one embodiment, the concentrate comprises (or consists essentially of, or consists of) (i) hydroxyacetophenone, (ii) at least one of vitamin B5, vitamin C, and vitamin E, (iii) at least one of 1,3-propanediol and a mastic extract and (iv) water. In another embodiment, the concentrate comprises (or consists essentially of, or consists of) (i) hydroxyacetophenone, (ii) at least one of vitamin B5, vitamin C, and vitamin E (such as vitamin B5), (iii) 1,3-propanediol, and (iv) optionally, water. In yet another embodiment, the concentrate comprises (or consists essentially of, or consists of) (i) hydroxyacetophenone, (ii) at least one of vitamin B5, vitamin C, and vitamin E (such as vitamin B5), (iii) mastic water, and (iv) optionally, water. In yet another embodiment, the concentrate comprises (or consists essentially of, or consists of) (i) hydroxyacetophenone, (ii) at least one of vitamin B5, vitamin C, and vitamin E (such as vitamin B5), (iii) mastic oil, and (iv) optionally, water. In a preferred embodiment, the concentrate consists of (i) hydroxyacetophenone, (ii) vitamin B5, (iii) 1,3-propanediol, and (iv) optionally, water. In a more preferred embodiment, the concentrate consists of (i) 20% by weight of hydroxyacetophenone, (ii) 1% by weight of vitamin B5, and (iii) 80% by weight of 1,3-propanediol. In one embodiment, when the concentrate includes 4-hydroxyacetophenone and 1,3-propanediol, the concentrate does not contain 3-phenylpropanol, 1,2-hexanediol, 1,2-octanediol, or ethylhexylglycerin.

In one embodiment, the concentrate comprises (or consists essentially of, or consists of) (a) from about 10 to about 20% by weight of 4-hydroxyacetophenone, (b) from about 60 to about 80% by weight of 1,3-propanediol, and (c) from about 1 to about 5% by weight of at least one of vitamin B5, vitamin C, and vitamin E (such as vitamin B5).

DETAILED DESCRIPTION OF THE INVENTION

Definitions

As used herein, the term "about" represent an amount or condition near to the stated amount or condition that still performs a desired function or achieves a desired result. For example, the term "about" may refer to an amount or condition that deviates by no more than 10% (i.e., ±10%), by no more than 5%, by no more than 1%, by no more than 0.1%, or by no more than 0.01% from a stated amount or condition.

The term "hydroxyacetophenone" unless indicated otherwise refers to 4-hydroxyacetophenone.

The term "microorganisms" includes, but is not limited to, bacteria, fungi, yeasts, algae, insects, and pests.

The term "personal care products" refers to products intended for application to the human body, such as to skin, hair, and nails, including, but not limited to, shampoos, conditioners, creams, lotions (such as body lotions), cosmetics, and soaps.

Mastic Extract

A mastic extract is derived from a mastic tree (*Pistacia lentiscus*). Suitable mastic extracts include, but are not limited to, mastic oil, mastic water, and any combination of any of the foregoing.

Mastic oil can be obtained from mastic by, for example, steam distillation.

Mastic water can be obtained as a byproduct during the steam distillation of mastic, such as from the steam distillation of mastic resin (the resin of *Pistacia* lentiscus var. chia).

In one embodiment, the product contains from about 0.001 to about 10% by weight of mastic extract, such as from about 0.001 to about 4%, from about 0.01 to about 2%, from about 0.05 to about 2%, from about 0.1 to about 2%, or from about 0.1 to about 1% by weight of mastic extract, based upon 100% total weight of product. For example, the product may contain from about 0.1 to about 10% by weight of mastic oil, such as from about 0.2 to about 8% or from about 0.3 to about 5% mastic oil. The product may contain from about 0.1 to about 10% by weight of mastic water, such as from about 0.5 to about 8% or from about 1 to about 7% mastic water (e.g., from about 1 to about 2% by weight of mastic water).

Additional Natural or Naturally Derived Compounds and Other Antimicrobials

The methods, products and concentrates may optionally include one or more additional natural or naturally derived compounds and/or one or more other antimicrobials.

Suitable natural or naturally derived compounds include, but are not limited to, quinic acid or a salt thereof, ethyl lauroyl arginate (ELA) or a salt thereof (including ethyl lauroyl arginate HCl), p-anisic acid or a salt thereof (e.g., sodium p-anisate), caprylhydroxamic acid or a salt thereof, 1,3-propanediol (only all natural type), glycereth-2 cocoate, benzyl alcohol (naturally derived from *cassia*), glycerin, organic solvents (e.g., ethylhexyl glycerin, phenoxyethanol, caprylyl glycols, pentylene glycol (natural), phenethyl alcohol (natural), and hexylene glycol), organic acids (e.g., sorbic acid, benzoic acid, and citric acid), and any combination of any of the foregoing.

Suitable other antimicrobials (for example, synthetic antimicrobials) include, but are not limited to, pirotine olamine, and any combination of any of the foregoing.

Combinations

In one embodiment, the weight ratio of (i) hydroxyacetophenone and (ii) at least one of 1,3-propanediol and a mastic extract ranges from about 0.01:100 to about 100:0.01, preferably ranges from about 0.1:20 to about 20:0.1, such as from about 1:10 to about 10:1.

In one embodiment, the weight ratio of (i) hydroxyacetophenone and (ii) 1,3-propanediol ranges from about 1:1 to about 1:20, such as from about 1:1 to about 1:15 or from about 1:3 to 1:12 or from about 1:3 to about 1:4 (for example, 1:4 or 1:9). In another embodiment, the weight ratio of hydroxyacetophenone to 1,3-propanediol ranges from about 5:95 to about 30:50. In yet another embodiment, the weight ratio of hydroxyacetophenone to 1,3-propanediol ranges from about 5:95 to about 25:75.

In another embodiment, the weight ratio of (i) hydroxyacetophenone and (ii) mastic water ranges from about 1:1 to about 1:20, such as from about 1:5 to about 1:15 or from about 1:3 to 1:12 (for example, 1:4 or 1:9). In another embodiment, the weight ratio of hydroxyacetophenone to mastic water ranges from about 5:95 to about 30:50. In yet another embodiment, the weight ratio of hydroxyacetophenone to mastic water ranges from about 5:95 to about 25:75.

In yet another embodiment, the weight ratio of (i) hydroxyacetophenone and (ii) mastic oil ranges from about 1:1 to about 1:20, such as from about 1:5 to about 1:15 or from about 1:3 to 1:12 (for example, 1:4 or 1:9). In another embodiment, the weight ratio of hydroxyacetophenone to mastic oil from about 5:95 to about 30:50. In yet another embodiment, the weight ratio of hydroxyacetophenone to mastic oil ranges from about 5:95 to about 25:75.

In any embodiment described herein, the weight ratio of hydroxyacetophenone to the at least one of vitamin B5, vitamin C, and vitamin E can range from about 1:1 to about 50:1, such as from about 10:1 to about 30:1 (e.g., 20:1).

In yet another embodiment, the weight ratio of (i) hydroxyacetophenone to (ii) ethylhexylglycerin (if present) ranges from about 10:1 to about 3:1.

In yet another embodiment, the product contains (i) from about 0.001 to about 10% by weight of hydroxyacetophenone, such as from about 0.001 to about 4%, from about 0.01 to about 2%, from about 0.05 to about 2%, from about 0.1 to about 2%, or from about 0.1 to about 1% by weight of hydroxyacetophenone, based upon 100% total weight of product, and (ii) from about 0.001 to about 10% by weight of 1,3-propanediol and/or a mastic extract, such as from about 0.001 to about 4%, from about 0.01 to about 2%, from about 0.05 to about 2%, from about 0.1 to about 2%, or from about 0.1 to about 1% by weight of 1,3-propanediol and/or a mastic extract, based upon 100% total weight of product.

In yet another embodiment, the product contains an effective amount of (i) hydroxyacetophenone and (ii) one or more 1,3-propanediol and/or a mastic extract to inhibit microbial growth in the product.

In one embodiment, the product contains hydroxyacetophenone and 1,3-propanediol. The product may contain (i) from about 0.001 to about 10% by weight of hydroxyacetophenone, such as from about 0.001 to about 4%, from about 0.01 to about 2%, from about 0.05 to about 2%, from about 0.01 to about 1%, or from about 0.05 to about 0.5% by weight of hydroxyacetophenone, based upon 100% total weight of product, and (ii) from about 0.001 to about 10% by weight of 1,3-propanediol, such as from about 0.001 to about 4%, from about 0.01 to about 2%, from about 0.01 to about 1%, from about 0.01 to about 0.1%, or from about 0.02 to about 0.08% by weight of 1,3-propanediol, based upon 100% total weight of product.

In another embodiment, the product contains hydroxyacetophenone and mastic water. The product may contain (i) from about 0.001 to about 10% by weight of hydroxyacetophenone, such as from about 0.001 to about 4%, from about 0.01 to about 2%, from about 0.05 to about 2%, from about 0.01 to about 1%, or from about 0.05 to about 0.5% by weight of hydroxyacetophenone, based upon 100% total weight of product, and (ii) from about 0.001 to about 10% by weight of mastic water, such as from about 0.001 to about 4%, from about 0.01 to about 2%, from about 0.01 to about 1%, from about 0.01 to about 0.1%, or from about 0.02 to about 0.08% by weight of mastic water, based upon 100% total weight of product.

In yet another embodiment, the product contains hydroxyacetophenone and mastic water. The product may contain (i) from about 0.001 to about 10% by weight of hydroxyacetophenone, such as from about 0.001 to about 4%, from about 0.01 to about 2%, from about 0.05 to about 2%, from about 0.01 to about 1%, or from about 0.05 to about 0.5% by weight of hydroxyacetophenone, based upon 100% total weight of product, and (ii) from about 0.001 to about 10% by weight of mastic oil, such as from about 0.001 to about 4%, from about 0.01 to about 2%, from about 0.01 to about 1%, from about 0.01 to about 0.1%, or from about 0.02 to about 0.08% by weight of mastic oil, based upon 100% total weight of product.

In yet another embodiment, the product contains hydroxyacetophenone, 1,3-propanediol, and ethylhexylglycerin. The product may contain (i) from about 0.001 to about 5% by weight of hydroxyacetophenone, such as from about 0.001 to about 4%, from about 0.01 to about 2%, from about 0.05 to about 2%, from about 0.01 to about 1%, or from about 0.05 to about 0.5% by weight of hydroxyacetophenone, (ii) from about 0.001 to about 10% by weight of 1,3-propanediol, such as from about 0.1 to about 8%, from about 0.2 to about 6%, from about 0.2 to about 5%, from about 0.2 to about 0.4%, or from about 0.2 to about 3% by weight of 1,3-propanediol, and (iii) from about 0.001 to about 5% by weight of ethylhexylglycerin, such as from about 0.001 to about 4%, from about 0.01 to about 2%, from about 0.05 to about 2%, from about 0.01 to about 1%, or from about 0.05 to about 0.5% by weight of ethylhexylglycerin, based upon 100% total weight of product.

In one of any of the aforementioned embodiments, the product comprises from about 0.001 to about 2% by weight of the at least one of vitamin B5, vitamin C, and vitamin E, based upon 100% total weight of the product. In one embodiment, the product does not contain (a) a glycerol ester of an alkane carboxylic acid or (b) an oligoglycerol ester of an alkane carboxylic acids.

The product or concentrate also preferably comprises a synergistic protective amount of (i) hydroxyacetophenone and (ii) at least one of 1,3-propanediol and mastic extract (e.g., a synergistic protective amount against fungi or bacteria). In another preferred embodiment, the product or concentrate comprises a synergistic protective amount of (i) hydroxyacetophenone, (ii) at least one of vitamin B5, vitamin C, and vitamin E (such as vitamin B5), and (iii) at least one of 1,3-propanediol and mastic extract (e.g., a synergistic protective amount against fungi or bacteria). In yet another preferred embodiment, the product or concentrate comprises a synergistic protective amount of (i) hydroxyacetophenone, (ii) ethylhexylglycerin, (iii) 1,3-propanediol, and optionally (iv) at least one of vitamin B5, vitamin C, and vitamin E (such as vitamin B5) (e.g., a synergistic protective amount against fungi or bacteria).

Products

The products described above may be a solid or liquid. In a preferred embodiment, the products described herein (as well as the concentrates described herein) are substantially free or completely free of parabens (such as methylparaben, ethylparaben, and propylparaben), formaldehyde donors, and/or isothiazolinones. According to one embodiment, the product (or concentrate) contains less than about 2, 1.5, 1, 0.5, 0.4, 0.3, 0.25, 0.2, 0.15, 0.1, 0.09, 0.08, 0.07, 0.06, 0.05, 0.04, 0.03, 0.02, or 0.01% by weight of parabens, formaldehyde donors, and/or isothiazolinones, based upon 100% total weight of product (or concentrate). According to one embodiment, the product (or concentrate) does not contain a preservative effective amount of a preservative. According to yet another embodiment, the product (or concentrate) is all natural. According to yet another embodiment, the product contains less than a smelling or coloring effective amount of the mastic extract.

In another embodiment, the product is substantially free or completely free of artificial (or synthetic) preservatives. According to one embodiment, the product contains less than about 2, 1.5, 1, 0.5, 0.4, 0.3, 0.25, 0.2, 0.15, 0.1, 0.09, 0.08, 0.07, 0.06, 0.05, 0.04, 0.03, 0.02, or 0.01% by weight of synthetic preservatives, based upon 100% total weight of product.

In one embodiment, the product (for example, a shampoo) has a pH below about 8. In another embodiment, the product has a pH from about 3 to about 9.

In one embodiment, the product is not intended for oral administration to an animal (e.g., a human subject). In another embodiment, the product is other than a foodstuff, pharmaceutical, cosmetic, or nutritional supplement. For example, the product can be a household (e.g., personal care), industrial, or institutional product. In one preferred embodiment, the product is a personal care product, such as a shampoo, body lotion, conditioner, or soap.

The protectant, such as hydroxyacetophenone in combination with (b)(i) at least one of 1,3-propanediol and mastic extract and/or (b)(ii) at least one of vitamin B5, vitamin C, and vitamin E, may be incorporated into substrates susceptible to microbial growth as a protectant to inhibit microbial growth. Suitable substrates include, but are not limited to, a personal care product, such as a shampoo, conditioner, cream, lotion (such as body lotion), cosmetic, or soap; a household product, such as a fabric softener, laundry detergent, or hard surface cleaner; or an industrial product, such as paint, coatings, wood, textile, adhesive, sealant, leather, rope, paper, pulp, paper board, sheet rock, ceiling tiles, plastic, fuel, petroleum, oil, rubber working fluid, metal working fluid, starches (such as pet food starch), or mineral slurry, such as a slurry of clay, calcium carbonate, or titanium oxide ($TiO_2$).

Generally, the protectant, such as hydroxyacetophenone in combination with (b)(i) at least one of 1,3-propanediol and mastic extract and/or (b)(ii) at least one of vitamin B5, vitamin C, and vitamin E, acts quickly (e.g., reduces the microorganism (e.g., bacteria and/or fungi) count by 95, 99, 99.9, or 99.99% typically within an hour) and maintains efficacy (e.g., maintains less than 1,000 or 100 cfu/g) over long periods of time (e.g., for at least 7, 10, 14, or 28 days).

The protectant, such as that containing the hydroxyacetophenone in combination with (b)(i) at least one of 1,3-propanediol and mastic extract and/or (b)(ii) at least one of vitamin B5, vitamin C, and vitamin E, may include a solvent, such as water and water miscible solvents, including, but not limited to, alcohols (e.g., methanol, ethanol, propanol, iso-propanol, and butanol), glycols (e.g. glycerin, diglycerin, butylene glycol, butoxydiglycol, propylene glycol, and dipropylene glycol), esters, ethers, polyethers, and any combination of any of the foregoing. For example, the solvent may comprise water and one or more glycol and/or one or more alcohol, such as glycerin, phenoxyethanol, benzyl alcohol, or ethanol. A specific solvent system comprises water and a glycol, such as glycerin. A second specific solvent system comprises water and an alcohol, such as ethanol.

The protectant may be incorporated into an aqueous or oil-based system or an emulsion. A suitable solvent for an oil-based system is phenoxyethanol and/or benzyl alcohol.

In one embodiment, the protectant is comprised of all-natural products. The protectant can be a liquid or a solid (e.g., a powder).

To prepare a formulation containing the product of the present invention, a concentrate of the protectant may be first prepared. The concentrate may be prepared by mixing the individual components. The concentrate may include from about 0.01 to about 100% by weight of the protectant such as from about 5 to about 80% by weight of the protectant, based upon 100% total weight of concentrate. For a two-component protectant, the concentrate may contain from about 0.01 to about 99.99% by weight of the hydroxyacetophenone and from about 99.99% to about 0.01% by weight of at least one of 1,3-propanediol and mastic extract, based upon 100% total weight of concentrate. Alternatively, the two-component protectant may contain from about 0.01 to about 99.99% by weight of the hydroxyacetophenone and from about from about 0.01% (e.g., 0.1 or 0.2%) to about 4% by weight of at least one of vitamin B5, vitamin C, and vitamin E, based upon 100% total weight of concentrate, with any remainder being a solvent (such as water). For a three-component protectant, the concentrate broadly contains (i) from about 0.01 to about 99.99% by weight of the hydroxyacetophenone, (ii) from about 99.99% to about 0.01% by weight of at least one of 1,3-propanediol and mastic extract, and (iii) from about 0.01% (e.g., 0.1 or 0.2%) to about 4% by weight of at least one of vitamin B5, vitamin C, and vitamin E, based upon 100% total weight of concentrate.

One embodiment is a concentrate comprising from about 5 to about 50% by weight of hydroxyacetophenone and from about 50% to about 95% by weight of 1,3-propanediol, based upon 100% total weight of the concentrate. In one preferred embodiment, the concentrate comprises from about 5 to about 30% by weight of hydroxyacetophenone and from about 70% to about 95% by weight of 1,3-propanediol. In another preferred embodiment, the concentrate comprises from about 5 to about 20% by weight of hydroxyacetophenone and from about 80% to about 95% by weight of 1,3-propanediol. In a preferred embodiment, the concentrate comprises, consists of, or consists essentially of (i) from about 10 to about 30% by weight of hydroxyacetophenone and (ii) from about 70 to about 90% by weight of 1,3-propanediol. A more preferred embodiment is a concentrate comprising about 10% hydroxyacetophenone thereof and about 90% 1,3-propanediol. Another more preferred embodiment is a concentrate comprising about 20% hydroxyacetophenone thereof and about 80% 1,3-propanediol. In any of the aforementioned embodiments, the concentrate may include from about 0.01% (e.g., 0.1 or 0.2%) to about 4% by weight of at least one of vitamin B5, vitamin C, and vitamin E, based upon 100% total weight of concentrate. In one preferred embodiment, the concentrate comprises about 20% hydroxyacetophenone thereof, about 1% of at least one of vitamin B5, vitamin C, and vitamin E, and about 79% 1,3-propanediol. In a more preferred embodiment, the concentrate comprises about 20% hydroxyacetophenone thereof, about 1% vitamin B5, and about 79% 1,3-propanediol.

Another embodiment is a concentrate comprising from about 5 to about 50% by weight of hydroxyacetophenone and from about 50% to about 95% by weight of mastic water, based upon 100% total weight of the concentrate. In one preferred embodiment, the concentrate comprises from about 5 to about 30% by weight of hydroxyacetophenone and from about 70% to about 95% by weight of mastic water. In another preferred embodiment, the concentrate comprises from about 5 to about 20% by weight of hydroxyacetophenone and from about 80% to about 95% by weight of mastic water. A more preferred embodiment is a concentrate comprising about 10% hydroxyacetophenone thereof and about 90% mastic water. In any of the aforementioned embodiments, the concentrate may include from about 0.01% (e.g., 0.1 or 0.2%) to about 4% by weight of at least one of vitamin B5, vitamin C, and vitamin E, based upon 100% total weight of concentrate.

Yet another embodiment is a concentrate comprising from about 5 to about 50% by weight of hydroxyacetophenone and from about 50% to about 95% by weight of mastic oil, based upon 100% total weight of the concentrate. In one preferred embodiment, the concentrate comprises from about 5 to about 30% by weight of hydroxyacetophenone and from about 70% to about 95% by weight of mastic oil. In another preferred embodiment, the concentrate comprises from about 5 to about 20 or 30% by weight of hydroxyacetophenone and from about 80% to about 95% by weight of mastic oil. A more preferred embodiment is a concentrate comprising about 10% hydroxyacetophenone thereof and about 90% mastic oil. In any of the aforementioned embodiments, the concentrate may include from about 0.01% (e.g., 0.1 or 0.2%) to about 4% by weight of at least one of vitamin B5, vitamin C, and vitamin E, based upon 100% total weight of concentrate.

Yet another embodiment is a concentrate comprising hydroxyacetophenone, mastic water, and 1,3-propanediol. The concentrate may contain from about 5 to about 30% by weight of hydroxyacetophenone, from about 5% to about 95% by weight of mastic water, and from about 5 to about 95% by weight of 1,3-propanediol. In another embodiment, the concentrate comprises from about 5 to about 20% by weight of hydroxyacetophenone, from about 30% to about 85% by weight of mastic water, and from about 10 to about 40% by weight of 1,3-propanediol. In any of the aforementioned embodiments, the concentrate may include from about 0.01% (e.g., 0.1 or 0.2%) to about 4% by weight of at least one of vitamin B5, vitamin C, and vitamin E, based upon 100% total weight of concentrate. For example, the concentrate may comprise from about 5 to about 20 or 30% by weight of hydroxyacetophenone, from about 0.2 to about 4% by weight of at least one of vitamin B5, vitamin C, and vitamin E, from about 30% to about 85% by weight of mastic water, and from about 10 to about 40% by weight of 1,3-propanediol.

Yet another embodiment is a concentrate comprising hydroxyacetophenone, 1,3-propanediol, and ethylhexylglycerin. In one embodiment, the concentrate does not contain 3-phenylpropanol. In another embodiment, the concentrate does not contain 1,2-hexanediol or 1,2-octanediol. In yet another embodiment, the concentrate comprises from about 60 to about 80% by weight of 1,3-propanediol, from about 10 to about 25% by weight (such as from about 10 to about 20% by weight) of 4-hydroxyacetophenone, and from about 1 to about 15% by weight (such as from about 1 to about 10% by weight or from about 5 to about 15% by weight) of ethylhexylglycerin, based upon 100% total weight of concentrate. In any of the aforementioned embodiments, the concentrate may include from about 1% to about 5% by weight of at least one of vitamin B5, vitamin C, and vitamin E, based upon 100% total weight of concentrate. In any of the aforementioned embodiments, the concentrate may include from about 0.01% (e.g., 0.1 or 0.2%) to about 4% by weight of at least one of vitamin B5, vitamin C, and vitamin E, based upon 100% total weight of concentrate. For example, the concentrate may comprise about 69% by weight of 1,3-propanediol, about 20% by weight of 4-hydroxyacetophenone, about 10% by weight of ethylhexylglycerin, and about 1% by weight of vitamin B5 (or DL-panthenol), based upon 100% total weight of concentrate.

In one embodiment, the concentrate comprises (or consists essentially of, or consists of) (a) from about 10 to about 20% by weight of 4-hydroxyacetophenone, (b) from about 60 to about 80% by weight of 1,3-propanediol, and (c) from about 0.1% or 1% to about 5% by weight of at least one of vitamin B5, vitamin C, and vitamin E (such as vitamin B5).

Before use, the concentrate may be diluted, such as with the same solvent as was used in the concentrate, and/or incorporated into a product. Use dilutions of the composition typically include an effective amount of protectant to inhibit microbial growth (e.g., fungi growth).

Generally, use dilutions contain from about 0.0001% or 0.01% to about 2% by weight of the concentrate. According to one preferred embodiment, use dilutions contain from about 0.1 to about 1% by weight of the concentrate. In more preferred embodiments, the use dilution contains 0.2, 0.25 or 0.30% by weight of the concentrate.

According to another embodiment, the protectant is incorporated into a product at a concentration of about 0.1 to about 1 or 2% by weight, based upon 100% total weight of product.

Method of Inhibiting Microbial Growth

Another embodiment of the present invention is a method for killing and/or inhibiting the growth of microorganisms, such as bacteria (e.g., S. aureus (ATCC #6538), P. aeruginosa (ATCC #9027), and E. coli (ATCC #8739)) and/or fungi (including plant and tree fungi) (e.g., Candida albicans, Aspergillus niger and Phytophthora ramrum), on a substrate by applying an effective amount of the protectant to the substrate or incorporating an effective amount of the protectant into the substrate. The protectant may be applied to or incorporated into the substrate by any method known in the art including, but not limited to, brushing, dipping, soaking, vacuum impregnation, and pressure treatment.

The protectant may be prepared by mixing the components and optionally, one or more solvents, and/or adjuvants. The mixture may be heated and/or stirred to expedite mixing.

Example 1

The CTFA Preservative Challenge Test was performed on a shampoo containing the samples below against a mixture of fungi (C. albicans (ATCC #10231) and A. brasihensis (ATCC #16404)) having an initial count of $7.9 \times 10^5$ cfu/mL or a mixture of bacteria having an initial count of $4 \times 10^6$ cfu/mL. The shampoos inoculated with bacteria were allowed to stand for 14 days and the shampoos inoculated with fungi were allowed to stand for 7 days. The samples were evaluated for surviving organisms on day 7 for fungi-inoculated shampoos and days 7 and 14 for bacteria-inoculated shampoos.

The results are shown in the table below.

| | Day 7 Count | |
| --- | --- | --- |
| Sample | Mixed Bacteria (cfu/mL) | Mixed Fungi (cfu/mL) |
| 5% 1,3-propanediol | $5.2 \times 10^2$ | $9.2 \times 10^2$ |
| 0.35% hydroxyacetophenone | $3.2 \times 10^2$ | $1.5 \times 10^2$ |
| 1.8% 1,3-propanediol and 0.2% hydroxyacetophenone | <10 | <10 |

From the table, synergism for the combinations above against mixed bacteria in shampoo was calculated by the method described in C. E. Kull et al., "Mixtures of Quaternary Ammonium Compounds and Long-chain Fatty Acids as Antifungal Agents", Applied Microbiology, 9:538-541 (1961). The synergism value $(Q_A/Q_a + Q_B/Q_b)$ was determined. $Q_A$ and $Q_B$ are concentrations of the first and second components, respectively, (in percent by weight) in the mixture, which yielded 100% retardation of the bacteria and fungi, i.e., resulted in a plate count of <10 cfu/g after 7 days. $Q_a$ is the concentration of the first component alone (in percent by weight) required to yield 100% retardation of the bacteria or fungi. $Q_b$ is the concentration of the second component alone (in percent by weight) required to yield 100% retardation of the bacteria or fungi. When the value of $(Q_A/Q_a + Q_B/Q_b)$ is less than one, the mixture is synergistic. Values for $(Q_A/Q_a + Q_B/Q_b)$ of 1 and greater represent an additive effect and an antagonistic effect, respectively. Here, $(Q_A/Q_a + Q_B/Q_b)$ is $((1.8\%/>5\%) + (0.2\%/>0.35\%))$ or <0.93.

Accordingly, the mixture of 1.8% 1,3-propanediol and 0.2% hydroxyacetophenone is synergistic.

Example 2

Aqueous solutions containing 2% of one of the protectants below were prepared by mixing and stored in sealed containers at 50° C. for 4 weeks.

Protectant A: 20% 4-hydroxyacetophenone and 80% 1,3-propanediol

Protectant B: 20% 4-hydroxyacetophenone, 1% vitamin B5, and 79% 1,3-propanediol

After the 4 weeks of storage, the solution containing vitamin B5 (Protectant B) was clear and colorless, while the other solution (Protectant A) was dark (medium amber) due to degradation of the 4-hydroxyacetophenone.

All references, patent applications, and patents cited herein are hereby incorporated by reference.

The invention claimed is:

1. A concentrate consisting of (a) from about 20% to about 30% by weight of 4-hydroxyacetophenone and (b) from about 70% to about 80% by weight of 1,3-propanediol.

2. The concentrate of claim 1, wherein the concentrate consists of (a) about 20% by weight of 4-hydroxyacetophenone and (b) about 80% by weight of 1,3-propanediol.

\* \* \* \* \*